United States Patent
Arakawa et al.

(10) Patent No.: US 8,072,604 B2
(45) Date of Patent: Dec. 6, 2011

(54) APPARATUS FOR DETECTING PROPERTIES OF FUEL FOR WORKING MACHINE

(75) Inventors: Shuji Arakawa, Hiratsuka (JP); Hidenori Koizumi, Hiratsuka (JP)

(73) Assignee: Komatsu Ltd., Tokyo (JP)

( * ) Notice: Subject to any disclaimer, the term of this patent is extended or adjusted under 35 U.S.C. 154(b) by 202 days.

(21) Appl. No.: 12/308,707

(22) PCT Filed: May 30, 2007

(86) PCT No.: PCT/JP2007/060983
§ 371 (c)(1), (2), (4) Date: Dec. 22, 2008

(87) PCT Pub. No.: WO2008/004387
PCT Pub. Date: Jan. 10, 2008

(65) Prior Publication Data
US 2009/0303466 A1      Dec. 10, 2009

(30) Foreign Application Priority Data
Jul. 5, 2006   (JP) .................................. 2006-185197

(51) Int. Cl.
     *G01N 21/00*    (2006.01)
(52) U.S. Cl. ........................................ 356/436; 250/343
(58) Field of Classification Search .......... 356/432–440, 356/307, 409, 128–137; 250/343, 345, 341.4
     See application file for complete search history.

(56) References Cited

U.S. PATENT DOCUMENTS

| | | | |
|---|---|---|---|
| 5,073,178 A | | 12/1991 | Mimori et al. |
| 5,139,334 A | * | 8/1992 | Clarke ............................ 356/301 |
| 5,157,453 A | * | 10/1992 | Suzuki et al. .................. 356/128 |
| 5,245,870 A | * | 9/1993 | Hartel et al. .................... 73/149 |
| 5,328,355 A | * | 7/1994 | Kobayashi et al. ............. 431/10 |
| 5,595,163 A | * | 1/1997 | Nogi et al. ..................... 123/494 |
| 6,493,086 B1 | * | 12/2002 | McAndrew et al. .......... 356/437 |

(Continued)

FOREIGN PATENT DOCUMENTS

JP         358129235 A    *    8/1983

(Continued)

OTHER PUBLICATIONS

International Search Report mailed on Aug. 28, 2007 for the corresponding International patent application No. PCT/JP2007/060983 (English translation enclosed).

(Continued)

*Primary Examiner* — Hoa Pham
(74) *Attorney, Agent, or Firm* — Posz Law Group, PLC

(57) ABSTRACT

An apparatus for detecting a property of fuel detects the property of fuel at the time of fuel supply. A measuring chamber member is provided to a fuel tank. The greater portion of fuel supplied from a fuel supply nozzle falls down from a fuel supply aperture via a flow outlet into the fuel tank. However, a part of the fuel remains in a measuring space defined between a portion below the flow outlet and a bottom portion. A fuel property detection sensor is fitted to a main body so as to oppose the measuring space. When application of a cap to the fuel supply aperture has been detected by a fuel supply cap sensor, if increase of the remaining fuel amount has been detected by a remaining fuel amount sensor, or if the engine is started, a controller measures the property of the fuel with the fuel property detection sensor.

17 Claims, 16 Drawing Sheets

U.S. PATENT DOCUMENTS

| | | | |
|---|---|---|---|
| 7,456,969 B2 * | 11/2008 | Chabanis et al. | 356/437 |
| 2007/0175271 A1 * | 8/2007 | Pividori et al. | 73/113 |
| 2007/0266762 A1 * | 11/2007 | Rumpf | 73/1.73 |
| 2009/0034901 A1 * | 2/2009 | Takabayashi et al. | 385/12 |

FOREIGN PATENT DOCUMENTS

| | | |
|---|---|---|
| JP | 02-20146 U | 2/1990 |
| JP | 2-181064 A | 7/1990 |
| JP | 02-139340 U | 11/1990 |
| JP | 2003-148136 A | 5/2003 |
| JP | 2004-219269 A | 8/2004 |
| JP | A-2005-076543 | 3/2005 |
| JP | 2005-098175 A | 4/2005 |

OTHER PUBLICATIONS

Office Action mailed Sep. 6, 2011 in corresponding JP application No. 2006-185197 (and English translation).

* cited by examiner

APPARATUS FOR DETECTING PROPERTIES OF FUEL FOR WORKING MACHINE

TECHNICAL FIELD

The present invention relates to an apparatus for detecting a property of the fuel for a working machine.

BACKGROUND ART

As working machines, various types of working machines are known, such as, for example, hydraulic shovels and wheel loaders and so on, and haulage vehicles such as dump trucks and so on. In order to reduce the costs of fuel, these vehicles are equipped with diesel engines, and diesel oil is used as the fuel. Although many users of working machines use normal diesel oil, sometimes some other fuel, such as kerosene or the like, is used in an unauthorized manner by being mixed in with the diesel oil. This is because kerosene and the like are cheaper in price than diesel oil.

However, since in recent years it is a strong requirement upon companies to address themselves to environmental problems, accordingly the makers of working machines and so on control their diesel engines at a high level of sophistication, and design the main components thereof, in order to reduce the negative impact upon the environment. This type of high level engine control assumes as a premise that normal diesel oil is being used as the fuel. Accordingly, if kerosene which includes a lower amount of oil as compared to diesel oil or an inferior fuel which includes impurities is used, then, while it is not possible to obtain the anticipated engine performance, also there is a possibility that damage may be caused to the fuel injection system or the like of the engine, and there is a possibility that the life of the engine may be decreased.

Thus, techniques have been proposed for detecting properties of the fuel. As a first such prior art technique, a method is known of discriminating whether or not normal diesel oil is being used, on the basis of the amount of sulfur oxide which is included in the exhaust gases of the engine (see Patent Document #1). And, as a second such prior art technique, a method is known of discriminating between diesel oil and kerosene on the basis of the difference in specific gravity between diesel oil and kerosene (see Patent Document #2).

Patent Document #1: Japanese Laid-Open Patent Publication 2004-219269;
Patent Document #2: Japanese Laid-Open Patent Publication Heisei 2-20146.

DISCLOSURE OF THE INVENTION

Problems to be Solved by the Invention

With these prior art techniques described in the above documents, in order to detect a property of the fuel which has already been supplied into the fuel tank, a property is detected of this fuel which consists of a mixture of normal fuel and inferior fuel. Accordingly, if the inferior fuel has been supplied in a state in which a certain amount of the normal fuel still remains within the fuel tank, then the proportion of the inferior fuel which is included in the remaining fuel amount decreases, and therefore the accuracy of detection of the fuel property also decreases.

The present invention has been conceived in consideration of the problem described above, and its object is to provide an apparatus for detecting a property of the fuel which is supplied to a working machine, which is capable of detecting the property of the fuel more accurately. Another object of the present invention is to provide an apparatus for detecting a property of the fuel which is supplied to a working machine, which is capable of detecting the property of the fuel which is supplied into the fuel tank at the time of fuel supply in a stable manner. Yet further objects of the present invention will become clear from the following description of preferred embodiments thereof.

Means for Solving the Problems

According to one aspect of the present invention, an apparatus for detecting a property of the fuel for a working machine is an apparatus for detecting a property of fuel which detects a property of fuel supplied to an engine of a working machine, characterized in that: a measuring chamber is provided to a fuel tank for containing a portion of the fuel which flows thereinto; and a fuel property detection means is provided to the measuring chamber, and detects the property of the fuel and outputs a detection signal.

In a preferred embodiment, the measuring chamber includes a tubular main body with a bottom, a fuel supply aperture which is provided upon an aperture surface of the main body, and a flow outlet, provided upon a side surface of the main body, for flowing out fuel which has flowed in from the fuel supply aperture into the fuel tank.

In a preferred embodiment, a drain aperture is provided in a bottom portion of the main body, for discharging fuel contained within the main body into the fuel tank.

In a preferred embodiment, the fuel property detection means is positioned between the flow outlet and the drain aperture, and is fitted to the main body.

In a preferred embodiment, the fuel property detection means detects the property of the fuel contained within the measuring chamber, when a measurement timing has arrived which is set at the time of supply of fuel into the fuel tank.

In a preferred embodiment, the measurement timing is either a fuel supply start timing at which the supply of fuel into the fuel tank is started, or a fuel supply end timing at which the supply of fuel into the fuel tank is ended.

In a preferred embodiment, a cap opening and closing detection means is provided which detects the open/closed state of a fuel supply cap which caps off the fuel supply aperture, and the arrival of the measurement timing is detected on the basis of a signal from this cap opening and closing detection means.

In a preferred embodiment, this opening and closing detection means detects whether or not the fuel supply cap is fitted by a non-contact method.

In a preferred embodiment, a nozzle detection means is provided in the neighborhood of the fuel supply aperture for detecting whether or not a fuel supply nozzle is inserted into the fuel supply aperture, and the arrival of the measurement timing is detected, if this nozzle detection means has detected the fuel supply nozzle.

In a preferred embodiment, a remaining fuel amount detection means is provided for detecting the amount of fuel remaining within the fuel tank, and the arrival of the measurement timing is detected if the remaining fuel amount detection means detects increase of the amount of fuel remaining within the fuel tank.

In a preferred embodiment, a cap opening and closing detection means is provided which detects the open/closed state of a fuel supply cap which caps off the fuel supply aperture, and the arrival of the measurement timing is detected if both a state in which the fuel supply cap has been removed and also a state in which it has been fitted have been detected by the cap opening and closing means, and moreover if the engine has been started.

In a preferred embodiment, there is further included a cap opening and closing detection means for detecting the open/closed state of a fuel supply cap which caps off the fuel supply aperture, and a remaining fuel amount detection means for detecting the amount of fuel remaining in the fuel tank; and the arrival of the measurement timing is detected, if both a state of removal and a state of fitting of the fuel supply cap have been detected by the cap opening and closing detection means, and moreover increase of the amount of fuel remaining within the fuel tank has been detected by the remaining fuel amount detection means.

In a preferred embodiment, the arrival of the measurement timing is detected if the fuel property detection means has detected the presence of fuel.

In a preferred embodiment, the fuel property detection means is constituted as an optical type fuel property detection means which detects the property of the fuel on the basis of the index of refraction of a light beam, and is adapted to detect the property of the fuel if the presence of fuel has been detected by change of refractive index.

Advantages of the Invention

According to the present invention, it is possible to detect the property of the fuel at the time of fuel supply. Due to this, it is possible to detect the property of the fuel with better accuracy, than in the case in which this detection is performed after the fuel which is the subject of detection has been mixed in with fuel already present within the fuel tank.

Since, according to the present invention, the measuring chamber is provided which contains a portion of the fuel which is supplied at the time of fuel supply, and since the fuel property detection means is provided to this measuring chamber, accordingly it is possible to detect the property of the fuel in a more stable state, than in the case of directly detecting the property of the fuel as it falls down within the fuel tank.

Since, according to the present invention, the drain aperture is provided for discharging the fuel within the measuring chamber into the fuel tank, accordingly it is possible to discharge the fuel within the measuring chamber into the fuel tank after the detection of the property of the fuel has been completed, and thereby to utilize all of the fuel without any useless wastage thereof.

Moreover since, according to the present invention, the fuel property detection means is provided between the flow outlet of the measuring chamber and the drain aperture, accordingly it is possible to detect the property of the fuel in a stable state in which the fuel is temporarily stagnated within the measuring chamber.

Since, according to the present invention, the cap opening and closing means is provided for detecting the open/closed state of the fuel supply cap, and since the arrival of the measurement timing is detected on the basis of the signal from this cap opening and closing detection means, accordingly it is possible to detect the timing of supply of fuel into the fuel tank.

And since, according to the present invention, the fuel property detection means detects the presence of fuel and also detects the property of that fuel, accordingly it is possible to perform both detection of the arrival of the timing for measurement and also detection of the property of the fuel with the single fuel property detection means, so that it is possible to simplify the structure and to manufacture it at low cost.

BEST MODE FOR CARRYING OUT THE INVENTION

In the following, embodiments of the present invention will be described in detail with reference to the figures. The apparatus for detecting a property of the fuel for a working machine according to this embodiment may be applied, for example, to a working machine such as a wheel loader or a truck or the like. As will be described hereinafter, at the time that fuel is supplied, the fuel property measurement device of this embodiment temporarily stores a portion of the fuel, and detects a property of the fuel which has been supplied after having properly prepared the measurement environment.

Embodiment One

Figure 1:
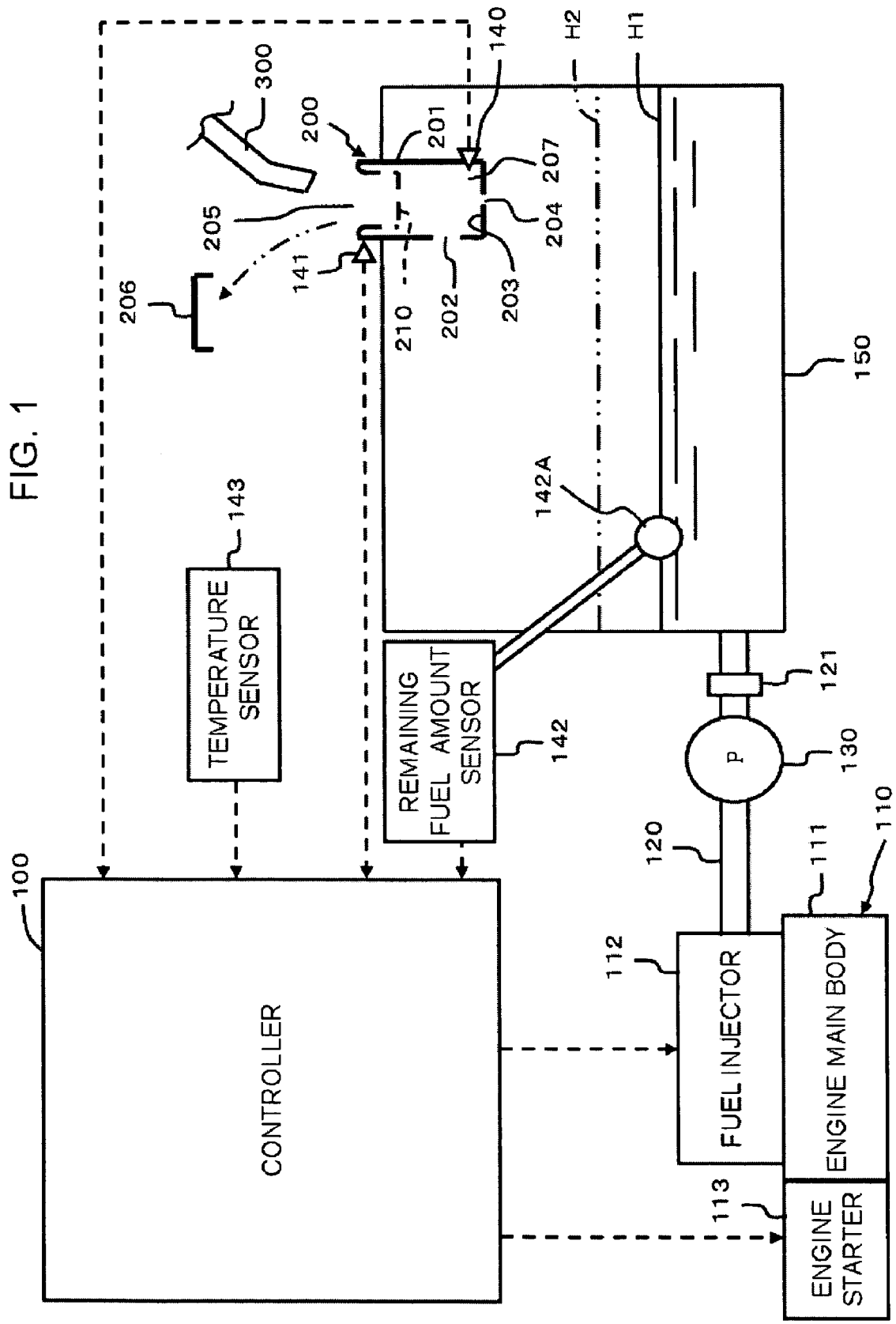
FIG. 1 is an explanatory figure showing the overall structure of an apparatus for detecting a fuel property.

A first embodiment of the present invention will now be explained. FIG. 1 is an explanatory figure showing the overall structure of an apparatus for detecting a property of fuel. This apparatus for detecting a property of fuel, for example, comprises a controller 100, a measuring chamber member 200, a fuel property detection sensor 140, a fuel supply cap sensor 141, a remaining fuel amount sensor 142, and a temperature sensor 143.

The controller 100 is a device for controlling the operation of the engine 110, and for controlling the operation of devices of various types which are provided to this working machine. Instead of this arrangement, it would also be acceptable to arrange to provide a dedicated controller which only discriminates the property of the fuel. Signals from various sensors 140 through 143 are inputted to the controller 100. The controller 100 is able to output measurement data relating to the fuel property and/or the results of discriminating the fuel to an external device. As such external devices there may be cited, for example, a management server which is connected to the controller 100 via a communication network, a printer or a display device which is connected to the controller 100, an alarm device which is connected to the controller 100, or the like.

The engine 100 may comprise, for example, an engine main body 111, a fuel injector 112, and an engine starter 113. The fuel injector 112 injects into the engine main body 111 fuel which has been supplied from a fuel tank 150 via a fuel conduit 120. The fuel pump 130 supplies fuel to the fuel injector 112 by sucking in fuel within the fuel tank 150 and discharging fuel into the fuel supply conduit 120. A fuel filter 121 is provided in the fuel supply conduit 120 for eliminating foreign matter and moisture in the fuel.

Next, various sensors 140 through 143 will be explained. A fuel property detection sensor 140 is a sensor which detects the property of the fuel and outputs a signal. This fuel property detection sensor 140 may, for example, detect the quality or the state of the fuel on the basis of physical qualities possessed by the fuel, such as specific gravity, refractive index, density, or the like. It is discriminated whether or not the fuel which is supplied into the fuel tank is diesel oil, according to the detection signal from the fuel property detection sensor 140.

A fuel supply cap sensor 141 is a device which detects whether or not a fuel supply cap 206 (refer to FIG. 5) is fitted to the fuel tank 150. The structure of this fuel supply cap sensor 141 will be described hereinafter with reference to FIG. 5.

A remaining fuel amount sensor 142 is a device which detects the amount of fuel within the fuel tank 150 and outputs a signal. A float 142A is provided within the fuel tank 150, and is displaced upwards and downwards by the liquid surface H1, H2 of the fuel within the fuel tank 150. The amount of displacement of this float 142A is converted by the remaining fuel amount sensor 142 into a remaining fuel amount. The liquid surface H1 in the figure shows a state immediately before the supply of fuel, while the surface H2 shows a state during the supply of fuel. It should be understood that the method of detecting the remaining fuel amount is not limited to the float type method described above. It would also be possible to employ some other structure for measuring the position of the liquid surface of the fuel, such as, for example, an optical sensor or an ultrasound sensor or the like.

A temperature sensor 143 is a device which, for example, detects the temperature of the fuel and outputs a signal. Instead of this, it would also be acceptable to utilize a structure in which the engine cooling water temperature or the external air temperature is detected. If the detection signal from the fuel property detection sensor 140 has a temperature dependence, then this temperature sensor 143 is provided. It would also be acceptable to provide a structure in which the fuel property detection sensor 140 and the temperature sensor 143 are integrated together. For example, it would be acceptable to house a temperature sensor 143 such as a thermistor, a thermocouple, a platinum resistance temperature sensor, or the like, internally within the fuel property detection sensor 140. It should be understood that it is not necessary to perform any temperature correction if the value of a physical property which does not depend upon temperature is employed.

Next, the structure of the fuel tank 150 and of the measuring chamber member 200 for measuring the property of the fuel will be explained. The measuring chamber member 200, which has a fuel supply aperture 205, is provided at the upper portion of the fuel tank 150. Normally, the fuel supply aperture 205 is closed off by a fuel supply cap 206. However, it is arranged for it to be possible to remove the fuel supply cap 206 at the time of supply of fuel, so that the fuel within the fuel tank 150 may be replenished by inserting a fuel supply nozzle 300 into the fuel supply aperture 205. Whether or not the fuel supply aperture 205 is closed off by the fuel supply cap 206 is detected by the fuel supply cap sensor 141.

The measuring chamber member 200 is a device which supplies the fuel property detection sensor 140 with a measurement environment for the fuel property by temporarily storing a portion of the fuel at the time of fuel supply. In other words, at the time of fuel supply, by temporarily stagnating a portion of the fuel to serve as a test specimen for measurement, the measuring chamber member 200 furnishes a more stable measurement environment, than if the fuel were immediately detected as it fell down from the fuel supply nozzle 300 within the fuel tank 150. A strainer 210 may be provided to the measuring chamber member 200, either integrally or capable of being fitted and removed.

Figure 2:
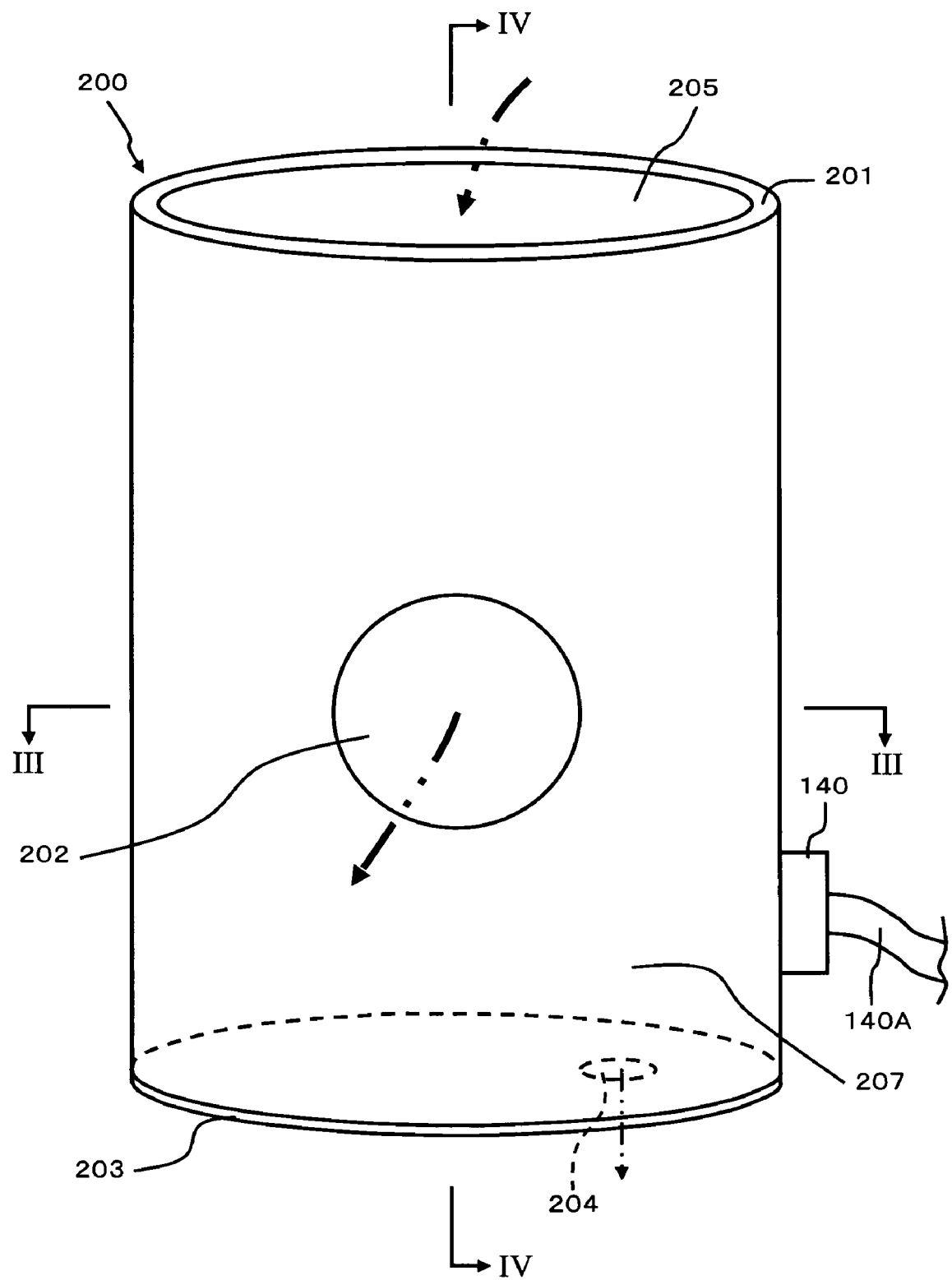
FIG. 2 is a perspective view of the external appearance of a measuring chamber member in its state with a strainer removed.

The structure of the measuring chamber member 200 will now be explained with reference to FIGS. 2 through 4. This measuring chamber member 200 may comprise, for example, a tubular main body 201 with a bottom, a flow outlet 202 which is provided on the side surface of the main body 201, a drain hole 204 which is provided in a bottom portion of the main body 201, and the fuel supply aperture 205 which is provided in the upper portion of the main body 201.

Figure 3:
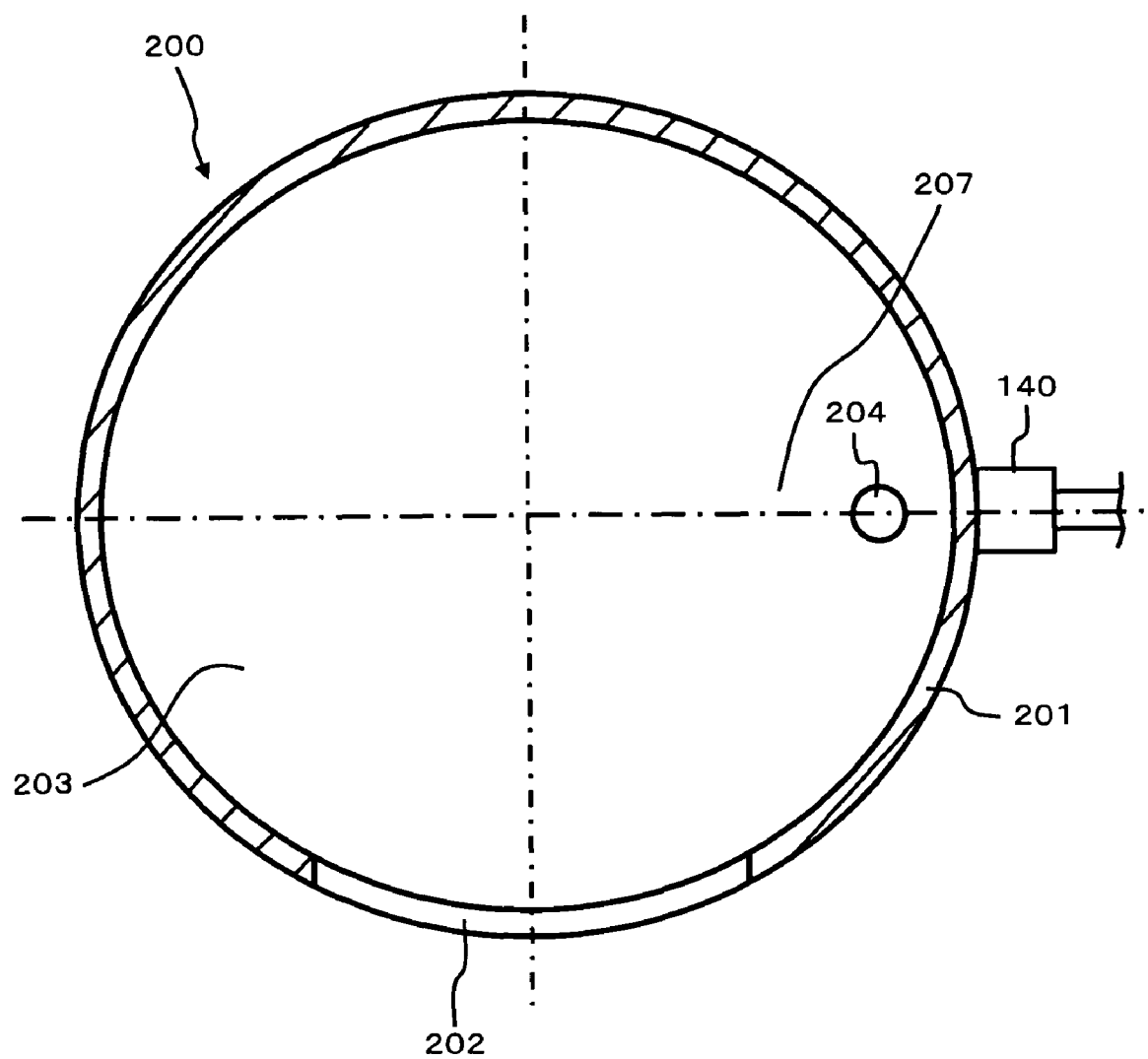
FIG. 3 is a sectional view shown in FIG. 2 by the arrow III-III.
Figure 4:
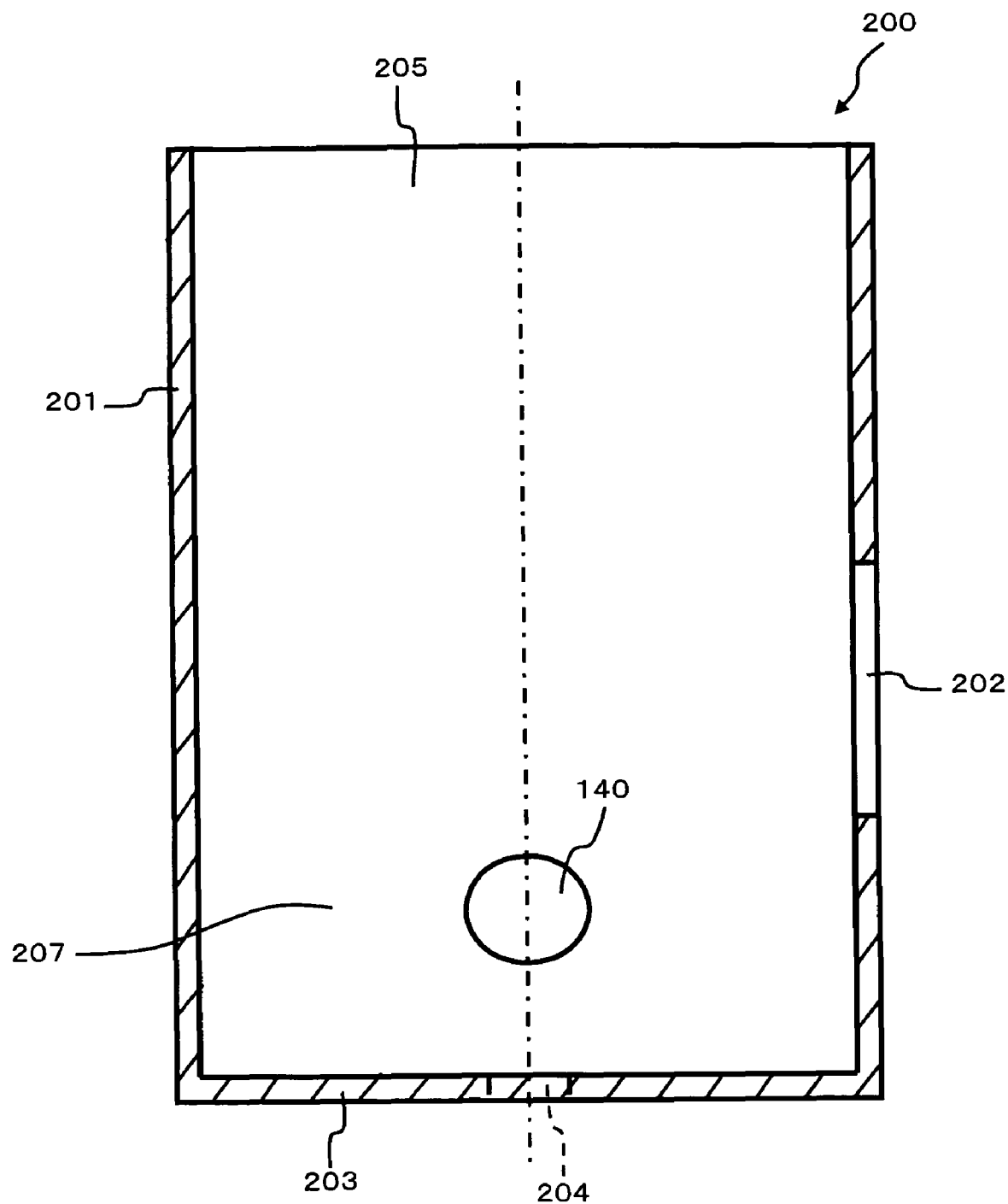
FIG. 4 is a sectional view shown in FIG. 2 by the arrow IV-IV.

In this embodiment, the main body 201 is formed in the shape of a cylinder having a circular horizontal cross section, as shown in the horizontal sectional view of FIG. 3. However this is not limitative; it would also be acceptable to arrange to form the main body 201 in the shape of a tube with corners, having a horizontal cross section which is triangular or quadrilateral, or has five or more corners.

On the side surface of the main body 201, the fuel property detection sensor 140 is fitted at a position which is at right angles to the position of the flow outlet 202. It should be understood that it would also be possible to utilize a structure in which the fuel property detection sensor 140 and the flow outlet 202 oppose one another.

The drain aperture 204 is provided in the bottom portion 203, for example at a position towards the side of the fuel property detection sensor 140. This is not limitative; it would also be acceptable to use a structure in which the drain aperture 204 is provided as separated from the fuel property detection sensor 140. A measuring space 207 is defined between the portion below the flow outlet 202 and the drain aperture 204, as shown in the vertical sectional view of FIG. 4. When the supply of fuel ends, a portion of the fuel which is supplied stagnates for a short time in this measuring space 207. The fuel property detection sensor 140 is fitted in the side surface of the main body 201, so as to oppose this measuring space 207.

At the time of fuel supply, the fuel supply cap 206 is removed, and the fuel supply nozzle 300 is inserted into the fuel supply aperture 205. The greater part of the fuel which is ejected from the fuel supply nozzle 300 flows out from the flow outlet 202 and falls down within the fuel tank 150. However, a portion of the fuel which is ejected from the fuel supply nozzle 300 stagnates within the measuring space 207 for a short time period only, even after the supply of fuel is completed.

The time period over which this fuel stagnates within the measuring space 207 may be adjusted according to the area of the drain aperture 204. If the area of the drain aperture 204 is set to be large, then the fuel within the measuring space 207 can be discharged into the fuel tank 150 rapidly. However, in this case, the time period over which the fuel property can be measured after the supply of fuel is completed becomes shorter. On the other hand, if the area of the drain aperture 204 is set to be small, then it is possible to make the fuel within the measuring space 207 stagnate for a comparatively long period of time, even after the supply of fuel is completed.

Figure 5:
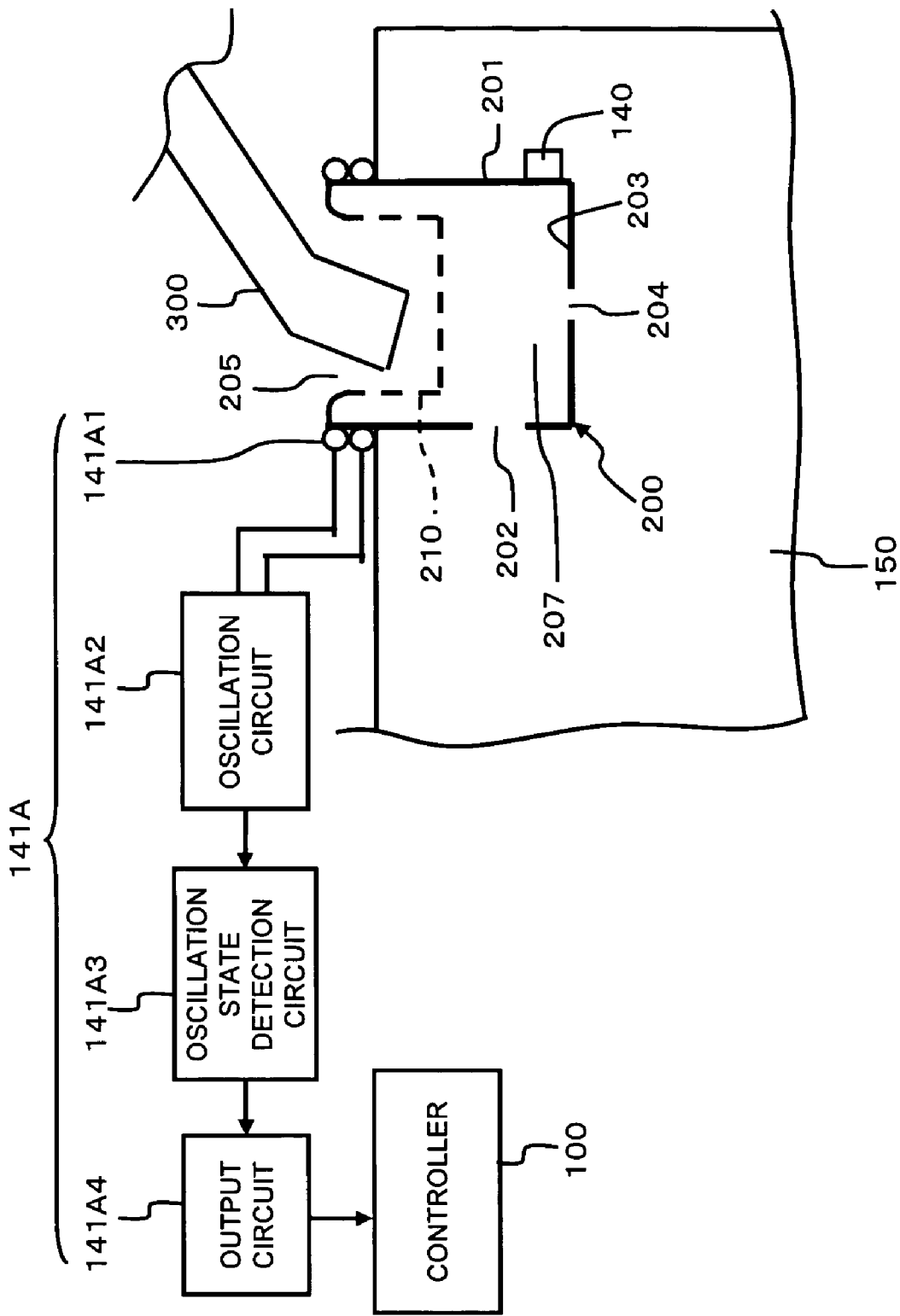
FIG. 5 is an explanatory figure showing an example of a fuel supply cap sensor.

FIG. 5 is a schematic figure showing a case in which the fuel supply cap sensor 141 is built as an inductive type sensor 141A. In the following explanation of FIG. 5, the fuel supply cap sensor 141 will be explained in terms of the structure of this inductive type nozzle detection sensor 141A.

The nozzle detection sensor 141A, for example, may comprise a detection coil 141A1, an oscillation circuit 141A2, an oscillation state detection circuit 141A3, and an output circuit 141A4. The detection coil 141A1 is wound around the circumferential surface of the main body 201 so as to surround the external circumference of the fuel supply aperture 205. The oscillation circuit 141A2 is coupled to the detection coil 141A1, and generates a high frequency magnetic field via the detection coil 141A1. The oscillation state detection circuit 141A3 is connected to the oscillation circuit 141A2, and detects stopping or attenuation of its oscillation. And the output circuit 141A4 is connected to the oscillation state detection circuit 141A3, and outputs an ON/OFF signal to the controller 100 when stoppage or attenuation of the oscillation is detected.

The operation of this inductive type nozzle detection sensor 141A will now be explained. When the fuel supply nozzle 300, which has at least an end portion which is made from metal, is inserted into the fuel supply aperture 205, due to the operation of electromagnetic induction, an induced electrical current flows in this metallic portion of the fuel supply nozzle 300, so that heating loss occurs. Due to this, the state of oscillation is stopped or attenuated. When the state of oscillation stops or is attenuated, the output circuit 141A4 outputs a signal to the controller 100. Accordingly, when the fuel supply nozzle 300 is inserted into the fuel supply aperture 205, this insertion of the fuel supply nozzle 300 can be detected, so that it is possible to detect the starting of the task of fuel supply. It should be understood that the above explanation is only an example, and is not limitative of the present invention. Some other type of sensor which can detect the fact that the fuel supply nozzle 300 has been inserted into the fuel supply aperture could also be utilized.

Figure 6:
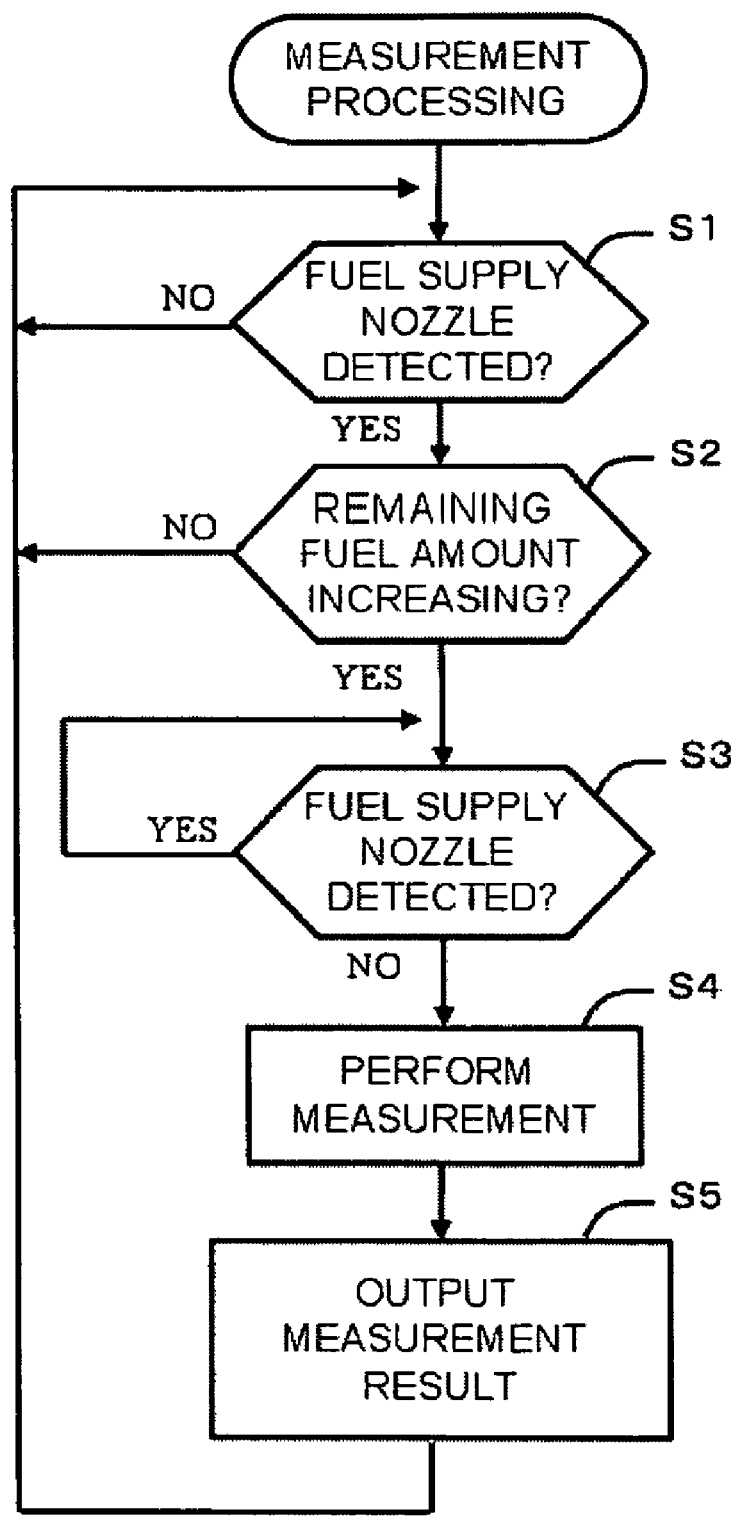
FIG. 6 is a flow chart showing processing for measurement of the fuel property.

Next, the processing for measurement of the property of the fuel will be explained with reference to the flow chart of FIG. 6. Upon detection by the fuel supply cap sensor 141 of the fact that the fuel supply nozzle 300 has been inserted into the fuel supply aperture 205 (YES in a step S1), the controller 100 makes a decision as to whether or not the remaining fuel amount is increasing, on the basis of the signal from the remaining fuel amount sensor 142 (a step S2).

If the remaining fuel amount is increasing (YES in the step S2), then the controller 100 decides that supply of fuel by the fuel supply nozzle 300 has been started. And the controller 100 decides, according to the fuel supply cap sensor 141, whether or not the fuel supply nozzle 300 has been pulled out from the fuel supply aperture 205 (a step S3).

If the remaining fuel amount is increasing (YES in the step S2), and moreover if the existence of the fuel supply nozzle 300 has ceased to be detected (NO in the step S3), then the controller 100 decides that the task of supplying fuel has ended, and starts the measurement of the property of the fuel with the fuel property detection sensor 140 (a step S4). And, by performing temperature correction and so on upon the detection signal from the fuel property detection sensor 140, the controller 100 outputs the result of measurement of the fuel property (a step S5).

According to this embodiment having the above structure, since the measuring chamber member 200 is incorporated to which the fuel property detection sensor 140 is provided, accordingly, at the time of supply of fuel, a portion of the fuel is stored in the measuring chamber member 200, so that it is possible for the property of this stored fuel to be detected by the fuel property detection sensor 140. Accordingly it is possible to obtain a more stable measurement environment as compared to a case in which the property of the fuel are detected while the fuel is falling down from the fuel supply nozzle 300 into the fuel tank 150, so that it is possible to enhance the accuracy of detection.

In this embodiment, since the drain aperture 204 is provided in the measuring chamber member 200, accordingly it is possible to discharge the fuel which is stored within the measuring chamber member 200 gradually into the fuel tank 150. Due to this, it is possible to ensure a sufficient time period for detecting the property of the fuel. Moreover, it is possible effectively to utilize the fuel whose property has been detected by discharging it into the fuel tank 150.

In this embodiment, the fuel property detection sensor 140 is provided so as to oppose the measuring space 207, between the flow outlet 202 and the drain aperture 204. Accordingly, this fuel property detection sensor 140 is able to detect the property of the fuel which is temporarily stored in the measuring space 207.

In this embodiment, the start and the end of the task of fuel supply are determined upon according to presence of the fuel supply nozzle 300 and according to the increase of the remaining fuel amount, and the property of the fuel is detected when the task of fuel supply has ended. Accordingly, it is possible to detect the property of the fuel which has been stored in the measuring space 207 while it is in a static state, so that it is possible to enhance the accuracy of detection.

In this embodiment, whether or not the fuel supply nozzle 300 has been inserted into the fuel supply aperture 205 is detected in a non-contact manner using the inductive type sensor 141A as the fuel supply cap sensor 141. Accordingly, it is possible to enhance the security and the durability, as compared to the case of using a switch which has mechanical contact points.

Embodiment Two

A second embodiment will now be explained on the basis of FIG. 7. For each of the embodiments described below, the explanation will concentrate on the points of difference from the first embodiment. In this embodiment, a photoelectric switch 141B is used as the fuel supply cap sensor 141.

Figure 7:
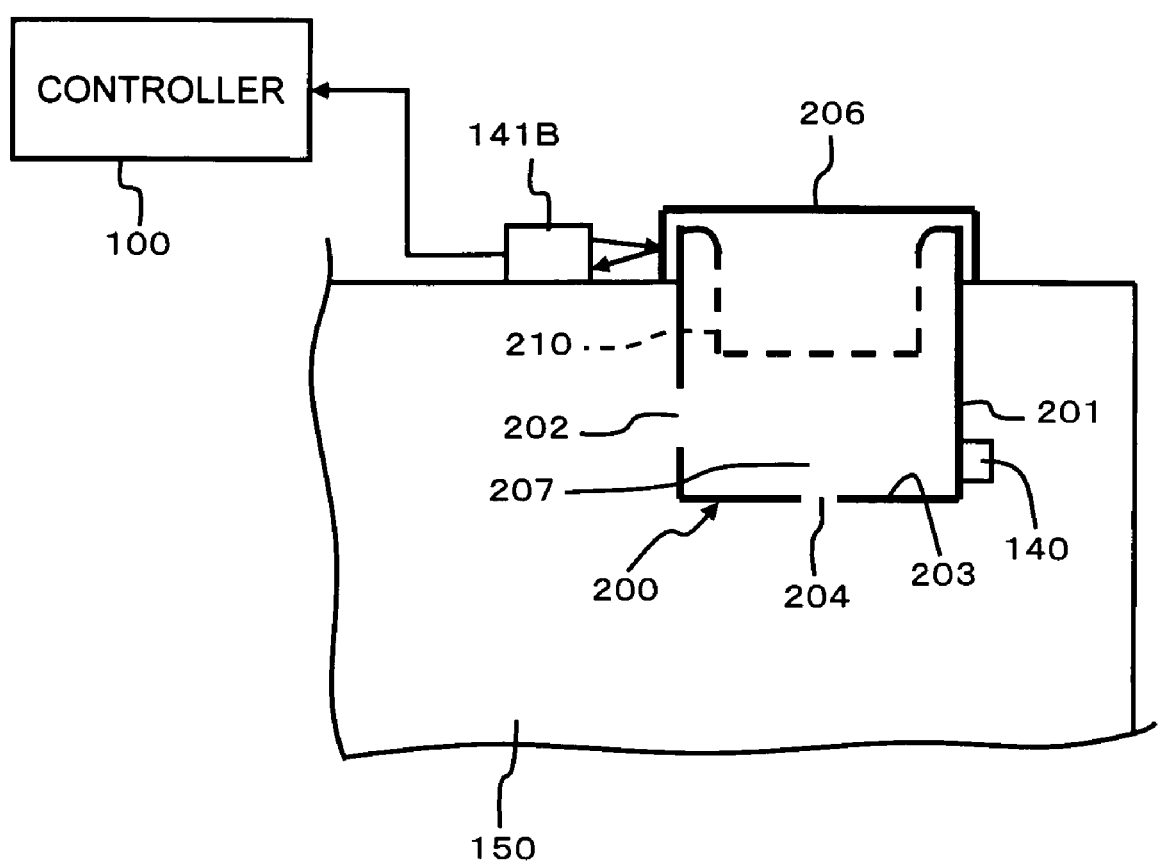
FIG. 7 is an explanatory figure showing the structure of a fuel supply cap sensor according to a second embodiment.

FIG. 7 is a schematic figure showing a photoelectric switch 141B, which serves as the fuel supply cap sensor in this embodiment. As shown in FIG. 7, this photoelectric switch 141B may, for example, be built as a reflective type photoelectric switch.

The photoelectric switch 141B irradiates light such as infrared rays or the like towards the side surface of the fuel supply cap 206, and receives the light reflected back from the fuel supply cap 206 and converts it into an electrical signal. Accordingly, the controller 100 is able to detect the presence or absence of the fuel supply cap 206 according to the ON/OFF signal from this photoelectric switch 141B. With this embodiment having the above structure, a similar advantageous effect may be obtained as in the case of the first embodiment above.

Embodiment Three

A third embodiment will now be explained with reference to FIG. 8. In this embodiment, a magnetic switch 141C is used as the fuel supply cap sensor 141.

Figure 8:
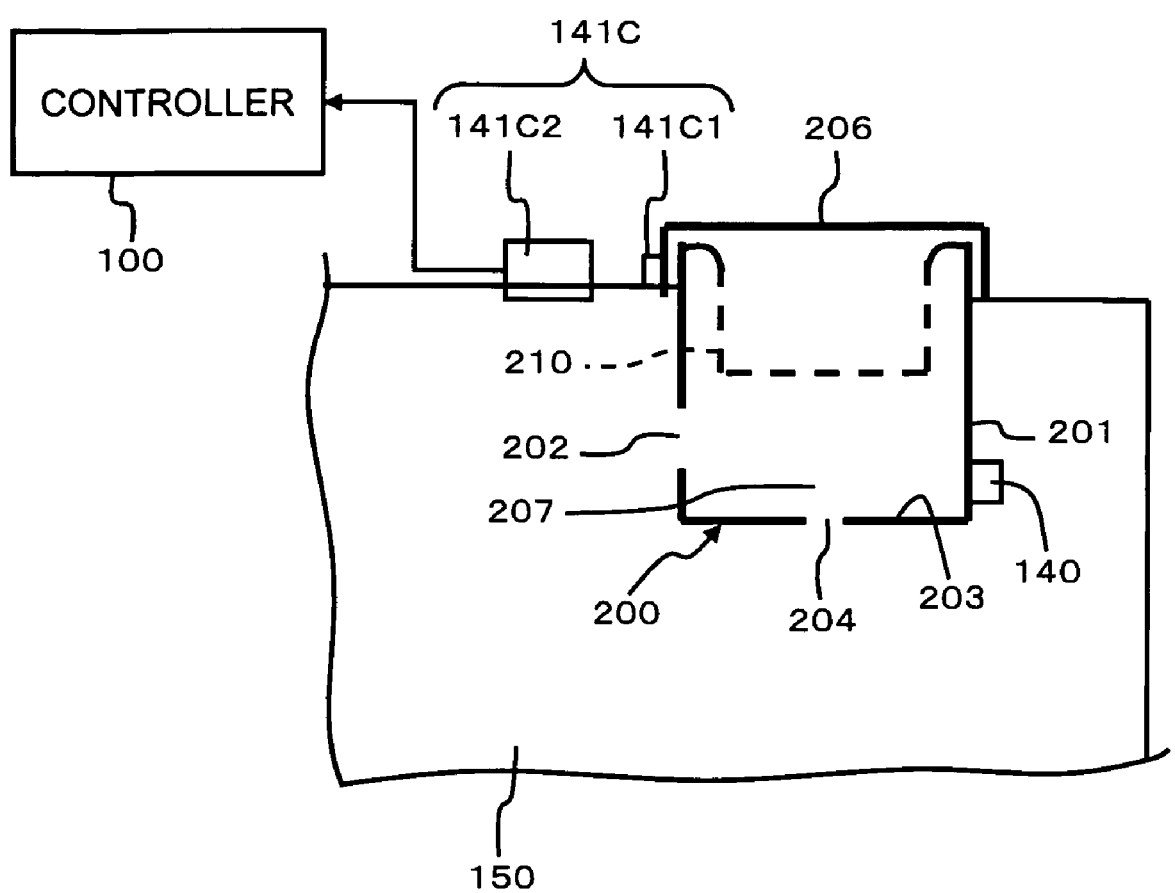
FIG. 8 is an explanatory figure showing the structure of a fuel supply cap sensor according to a third embodiment.

FIG. 8 is a schematic figure showing a magnetic switch 141C, which is the fuel supply cap sensor 141 according to this embodiment. A magnet 141C1 is provided upon the side surface of the fuel supply cap 206, and a Hall IC 141C2, which incorporates an internal Hall element, is provided so as to oppose the magnet 141C1.

The magnetic switch 141C detects change of the magnetic field due to shifting of the magnet 141C1, and outputs its detection signal to the controller 100. The controller 100 is thus able to detect the presence or absence of the fuel supply cap 206 on the basis of the signal from the magnetic switch 141C. With this embodiment having the above structure, a similar advantageous effect may be obtained as in the case of the first embodiment above.

Embodiment Four

Figure 9:
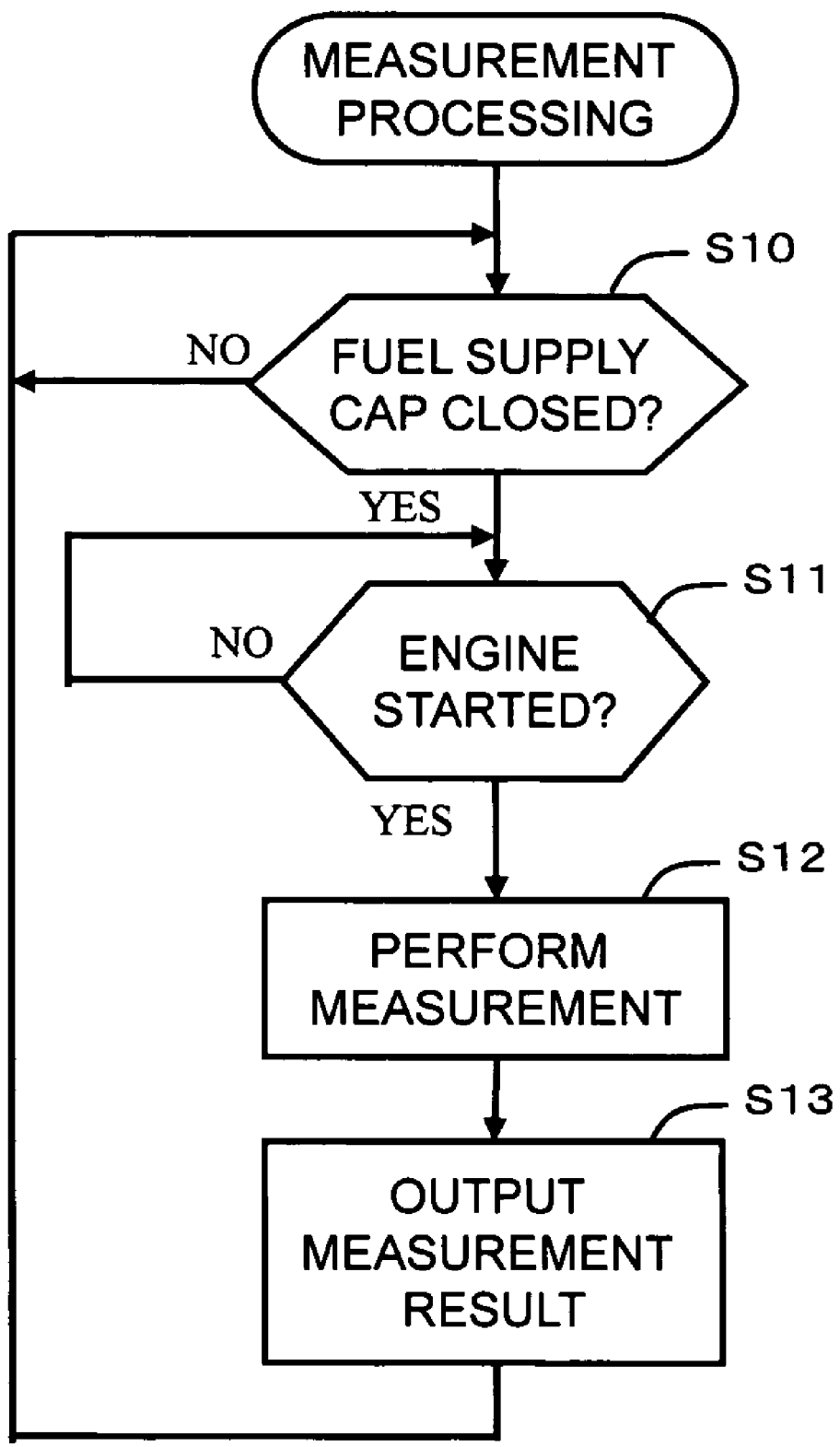
FIG. 9 is a flow chart showing processing for measurement of a fuel property according to a fourth embodiment.

A fourth embodiment will now be explained with reference to FIG. 9. FIG. 9 is a flow chart showing the processing for measurement of fuel property according to this embodiment. The controller 100 monitors whether or not the fuel supply aperture 205 is capped off with the fuel supply cap 206 (a step S10), and, if the fuel supply aperture is indeed capped off (YES in the step S10), then the controller 100 decides whether or not the engine has been started (a step S11). If engine starting is detected (YES in the step S11), then the controller 100 starts measurement of the property of the fuel with the fuel property detection sensor 140 (a step S12), and outputs the result of this measurement (a step S13).

Since, in this embodiment, if the fuel supply aperture 205 is capped with the fuel supply cap 206, and moreover the engine 110 has been started, then it is decided that the task of fuel supply has been completed, and measurement of the property of the fuel is performed, accordingly a similar advantageous effect is obtained as in the case of the first embodiment. However, it is only effective in the case that, after the supply of fuel has been completed, the engine 110 is started before the remaining fuel in the measuring space 207 is discharged from the drain aperture 204.

Embodiment Five

Figure 10:
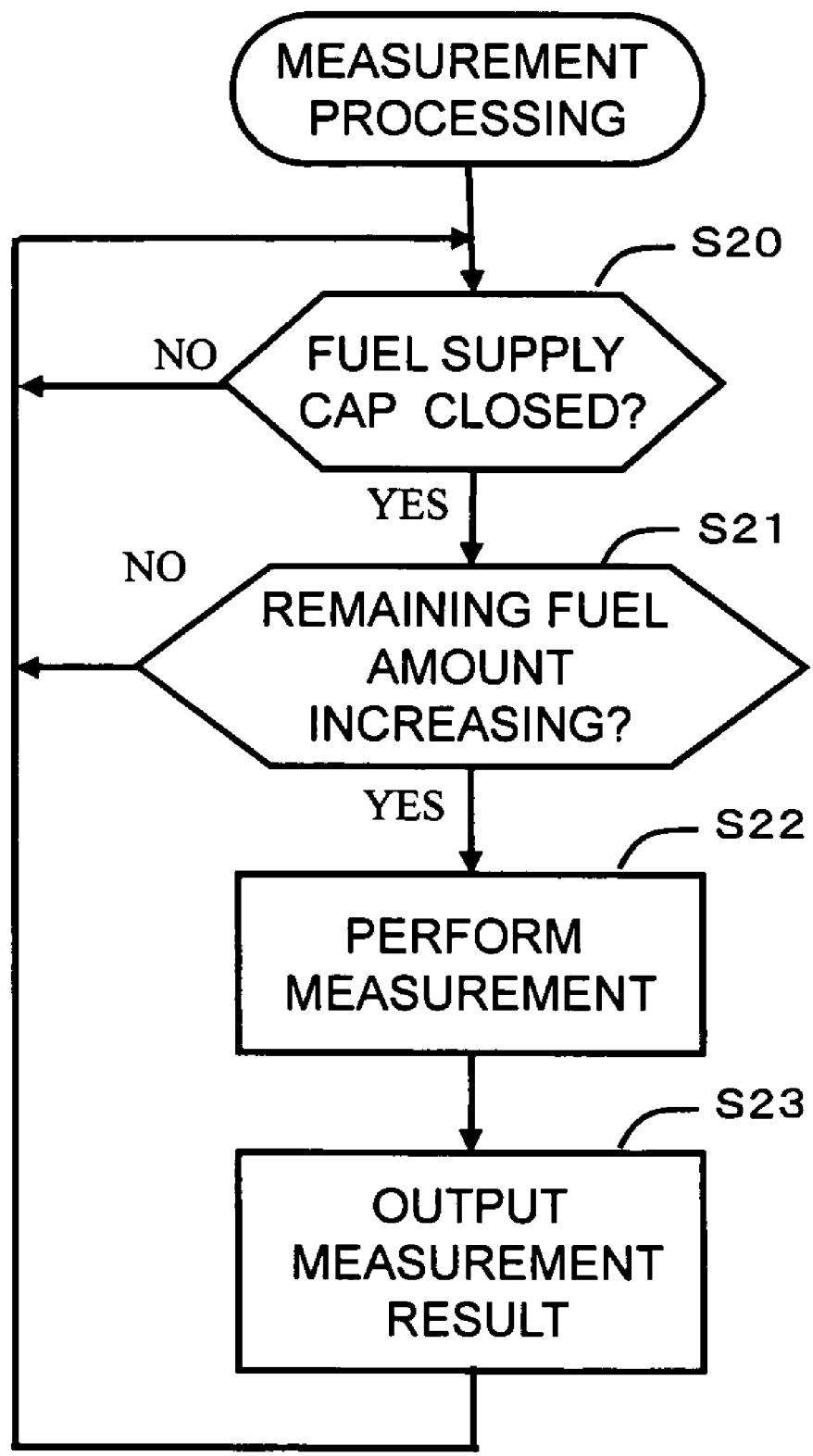
FIG. 10 is a flow chart showing processing for measurement of a fuel property according to a fifth embodiment.

A fifth embodiment will now be explained with reference to FIG. 10. FIG. 10 is a flow chart showing the processing for measurement of fuel property according to this embodiment. The controller 100 monitors whether or not the fuel supply aperture 205 is capped off with the fuel supply cap 206 (a step S20). If the fuel supply aperture 205 is capped off with the fuel supply cap 206 (YES in the step S20), then the controller 100 decides whether or not the remaining fuel amount has increased, upon the basis of the signal from the remaining fuel amount sensor 142 (a step S21).

If after the fuel supply cap 206 has been closed the remaining amount of fuel has increased (YES in the step S21), then the controller 100 starts the measurement of the property of the fuel with the fuel property detection sensor 140 (a step S22), and outputs the result of this measurement (a step S23). With this embodiment having the above structure, a similar advantageous effect may be obtained as in the case of the first embodiment above.

Embodiment Six

Figure 11:
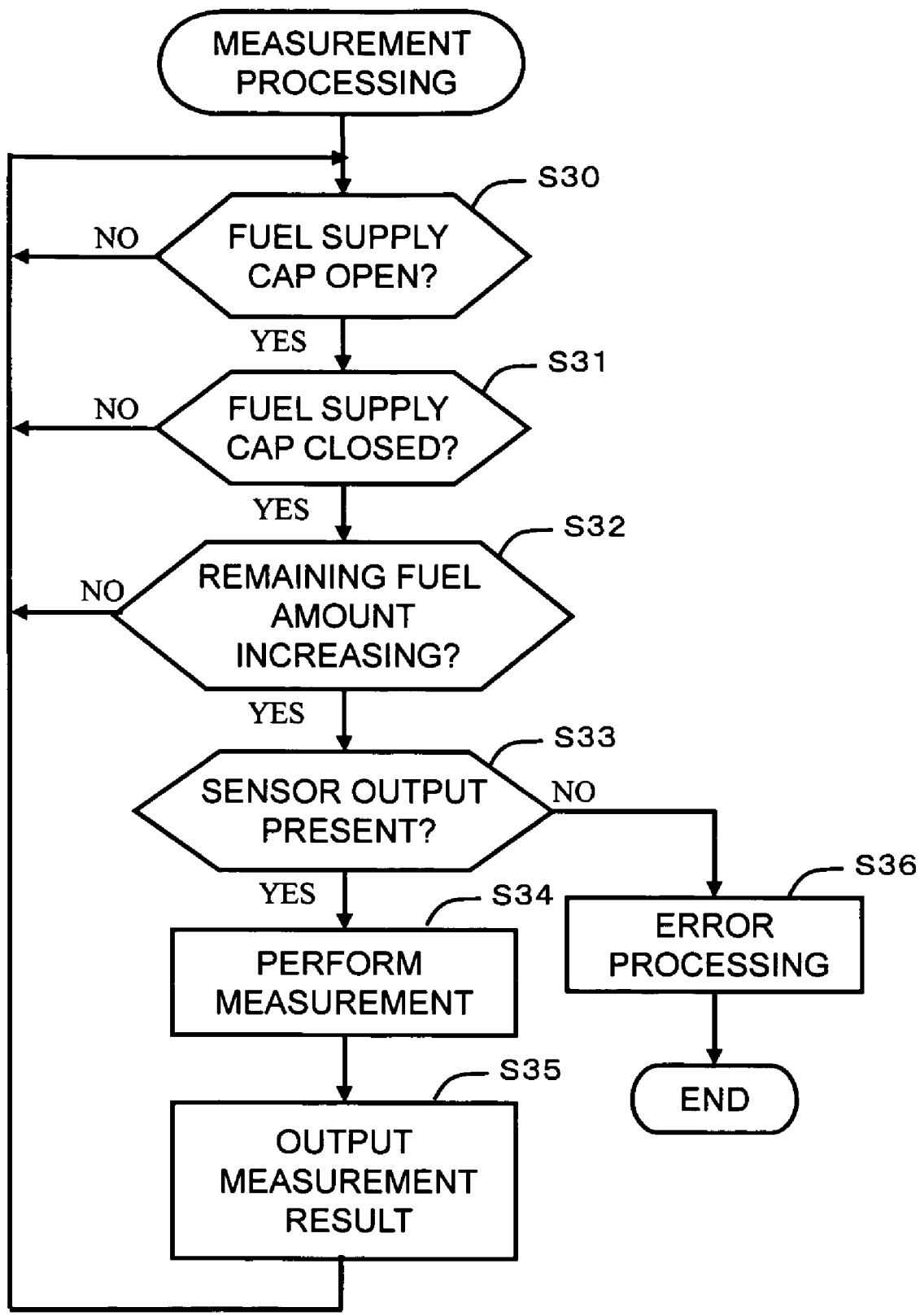
FIG. 11 is a flow chart showing processing for measurement of a fuel property according to a sixth embodiment.

A sixth embodiment will now be explained with reference to FIG. 11. FIG. 11 is a flow chart showing the processing for measurement of fuel property according to this embodiment. In this embodiment, the fuel property detection sensor 140 diagnoses whether or not it is operating normally.

First, the controller 100 decides whether or not the fuel supply cap 206 has been removed from the fuel supply aperture 205 (a step S30). If the fuel supply cap 206 has been removed (YES in the step S30), then the controller 100 makes a decision as to whether or not the fuel supply aperture 205 has been capped off with the fuel supply cap 206 (a step S31). And the controller 100 makes a decision as to whether or not the remaining fuel amount has increased, on the basis of the signal from the remaining amount of fuel sensor 142 (a step S32).

When the fuel supply aperture 205 has been opened and then closed, and moreover the remaining amount of fuel has increased, then it is decided that the task of supply of fuel has been completed, and moreover that the state now holds in which fuel supplied at the time of fuel supply is stagnated in the measuring space 207. Thus, the controller 100 makes a decision as to whether or not a signal is being outputted from the fuel property detection sensor 140 (a step S33).

If a signal is being outputted from the fuel property detection sensor 140 (YES in the step S33), then the controller 100 decides that the fuel property detection sensor 140 is operating normally. Accordingly, the controller starts the measurement of the property of the fuel with the fuel property detection sensor 140 (a step S34), and outputs the result of this measurement (a step S35).

On the other hand, if no signal is being outputted from the fuel property detection sensor 140 (NO in the step S33), then the controller 100 decides that it is the case that the fuel property detection sensor 140 has failed, or that it is the case that there is a breakage or the like in the signal line between the fuel property detection sensor 140 and the controller 100, and accordingly performs error processing (a step S36). As such error processing, there may be cited, for example, display of an error message which notifies the user of a fault with the fuel property detection sensor 140.

With this embodiment having the structure described above, the reliability is enhanced, because, before detecting the property of the fuel, diagnostics are performed in order to determine whether or not the fuel property detection sensor 140 is operating normally.

Embodiment Seven

Figure 12:
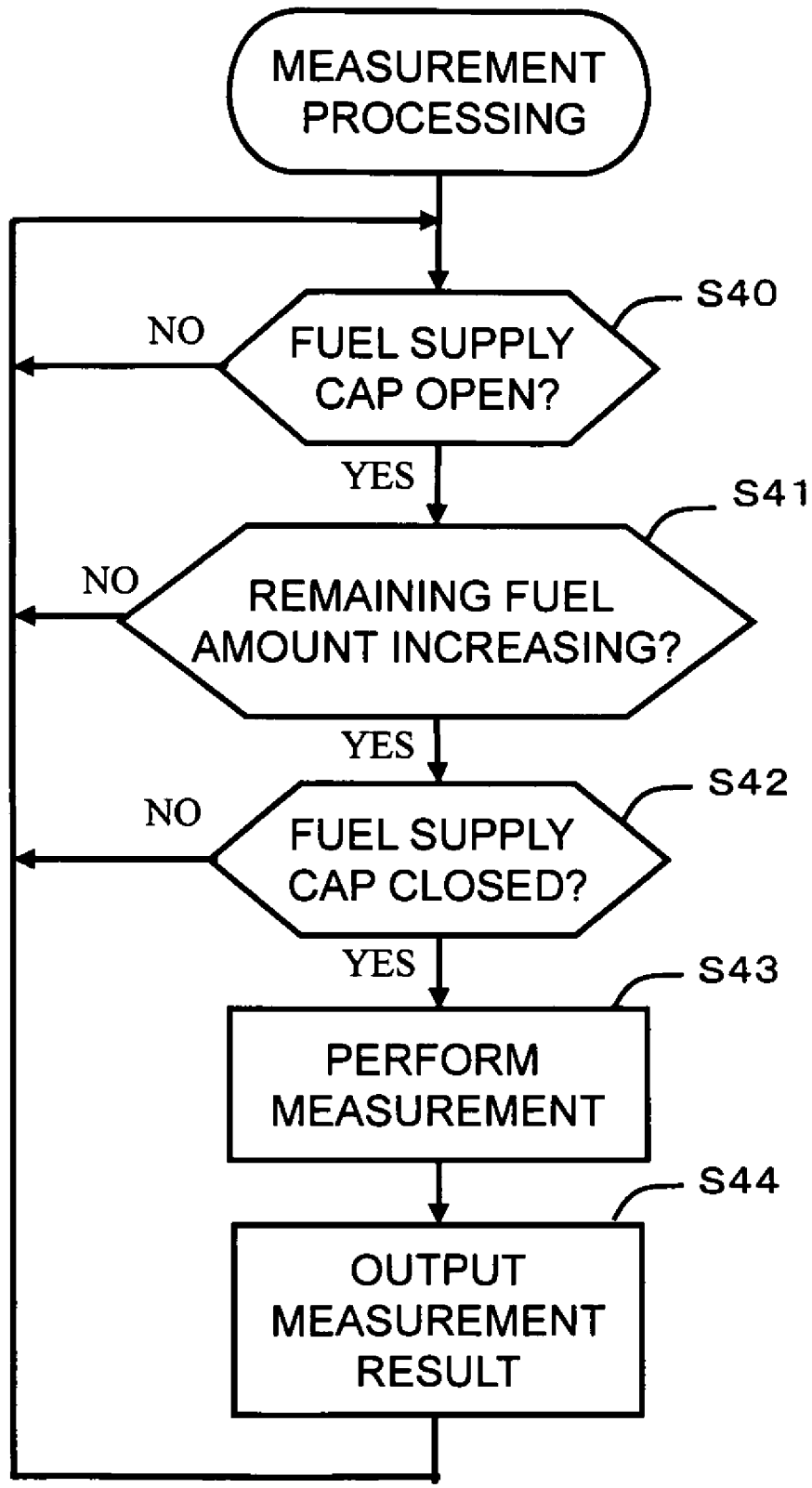
FIG. 12 is a flow chart showing processing for measurement of a fuel property according to a seventh embodiment.

A seventh embodiment will now be explained with reference to FIG. 12. FIG. 12 is a flow chart showing the processing for measurement of fuel property according to this embodiment. In this embodiment, the self-diagnosis of the fuel property detection sensor 140 is omitted.

In other words, the controller 100 decides whether or not the fuel supply cap 206 has been removed from the fuel supply aperture 205 (a step S40), and if the fuel supply cap 206 has been removed (YES in the step S40), then the controller 100 decides whether or not the remaining fuel amount is starting to increase (a step S41).

After the controller 100 has confirmed that the remaining fuel amount is increasing (YES in the step S42) [sic], then it makes a decision as to whether or not the fuel supply aperture 205 is capped off with the fuel supply cap 206 (a step S42). If the fuel supply aperture 205 is capped off with the fuel supply cap 206 (YES in the step S42), then the controller 100 starts the measurement of the property of the fuel with the fuel property detection sensor 140 (a step S43), and outputs the result of this measurement (a step S44). With this embodiment having the above structure, a similar advantageous effect may be obtained as in the case of the first embodiment above.

Embodiment Eight

Figure 13:
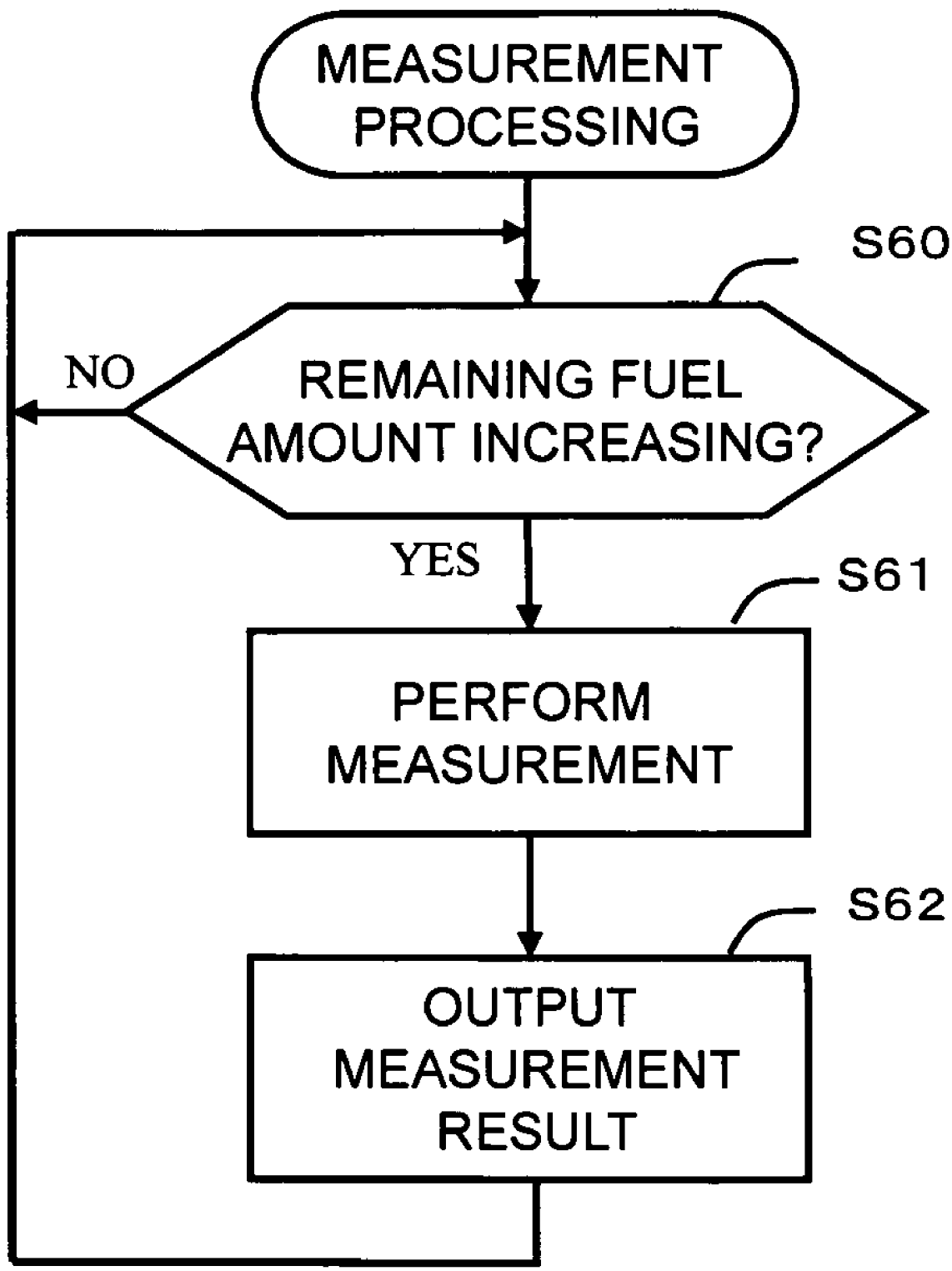
FIG. 13 is a flow chart showing processing for measurement of a fuel property according to an eighth embodiment.

An eighth embodiment will now be explained with reference to FIG. 13. FIG. 13 is a flow chart showing the processing for measurement of fuel property according to this embodiment. The controller 100 decides whether or not the remaining amount of fuel has increased, on the basis of the signal from the remaining fuel amount sensor 142 (a step S60). If the remaining amount of fuel has increased (YES in the step S60), then the controller 100 decides that the task of supply of fuel has been completed, and measures the property of the fuel which remains in the measuring space 207 with the fuel property detection sensor 140 (a step S61). And the controller 100 outputs the result of this measurement (a step S62).

With this embodiment having the above structure, a similar advantageous effect may be obtained as in the case of the first embodiment above. In addition thereto, since, in this embodiment, if the remaining amount of fuel has increased, the property of the fuel are detected after it has been decided that the task of supply of fuel has been completed, accordingly it is not necessary to provide any fuel supply cap sensor 141, and moreover it is possible to simplify the control structure.

Embodiment Nine

Figure 14:
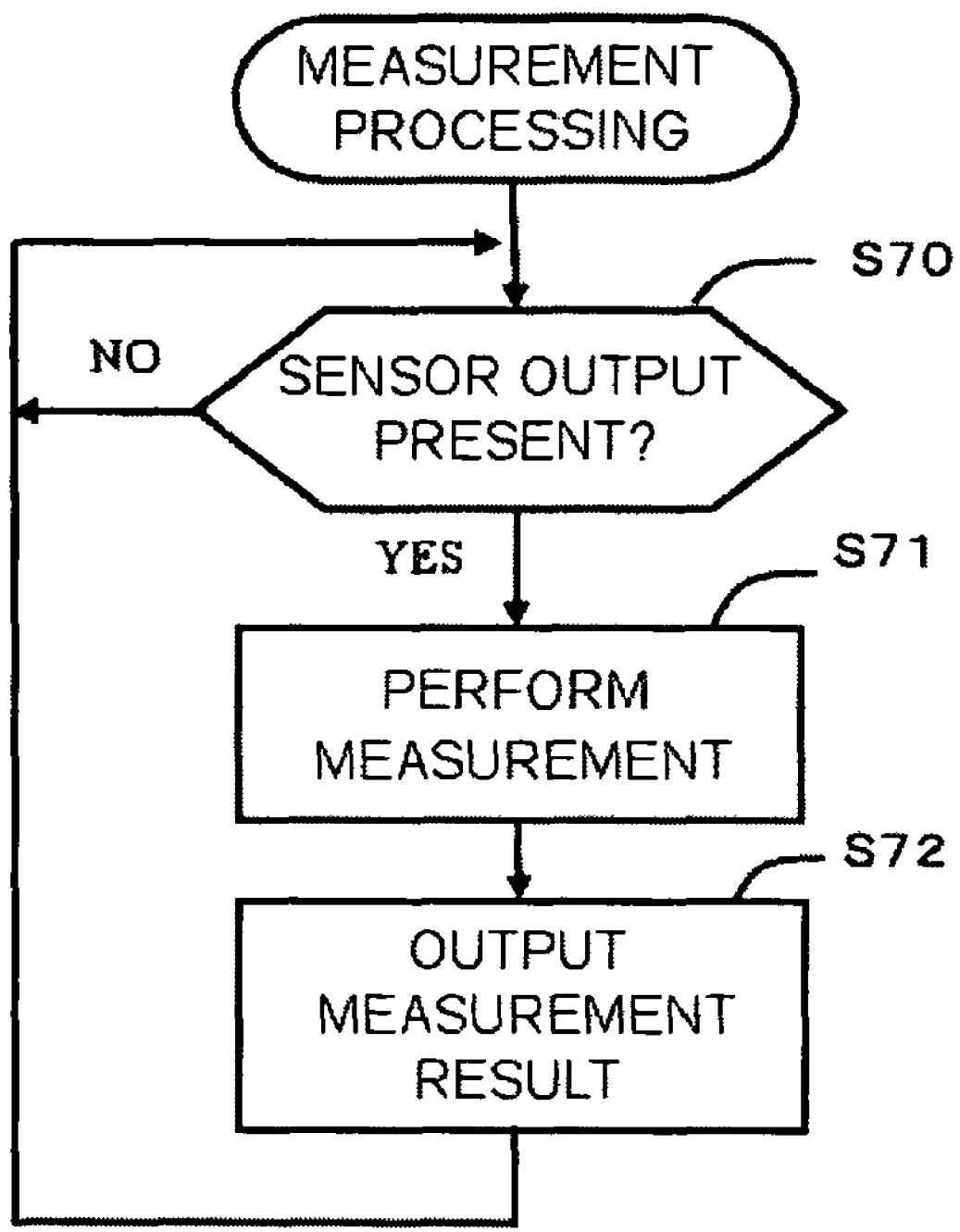
FIG. 14 is a flow chart showing processing for measurement of a fuel property according to a ninth embodiment.

A ninth embodiment will now be explained with reference to FIG. 14. FIG. 9 [sic] is a flow chart showing the processing for measurement of fuel property according to this embodiment. In this embodiment, the timing of measurement of the property of the fuel is decided upon the basis of the signal from the fuel property detection sensor 140.

The controller 100 decides whether or not any signal is being outputted from the fuel property detection sensor 140 (a step S70). If a signal is outputted from the fuel property detection sensor 140 (YES in the step S70), then it is considered that fuel is stagnating in the measuring space 207. Thus, the controller 100 starts the measurement of the property of the fuel with the fuel property detection sensor 140 (a step S71), and outputs the result of this measurement (a step S72).

As a condition for this embodiment and also for the sixth embodiment, the fuel property detection sensor 140 should have a structure such that it outputs signals of different levels, if fuel is present within the measuring space 207, and if no such fuel is present. For example, the level of the signal from the fuel property detection sensor 140 may be lower than some predetermined threshold value if no fuel is present within the measuring space 207, and the level of the signal from the fuel property detection sensor 140 may be higher than that predetermined threshold value if fuel is present within the measuring space 207. Accordingly, it is possible to decide upon the presence or the absence of fuel on the basis of the signal from the fuel property detection sensor 140. And, if the presence of fuel has been detected, the controller 100 may, for example, measure the property of the fuel by reading in the signal from the fuel property detection sensor 100 a plurality of times and by performing temperature correction and the like, and may output the result of this measurement.

With this embodiment having the above structure, a similar advantageous effect may be obtained as in the case of the first embodiment above. In addition thereto, since, in this embodiment, detection of the presence or absence of the fuel and also detection of the property of the fuel are both performed using the fuel property detection sensor 140, accordingly it is possible to simplify the overall structure, and it is possible to manufacture the system at a low cost.

Figure 15:
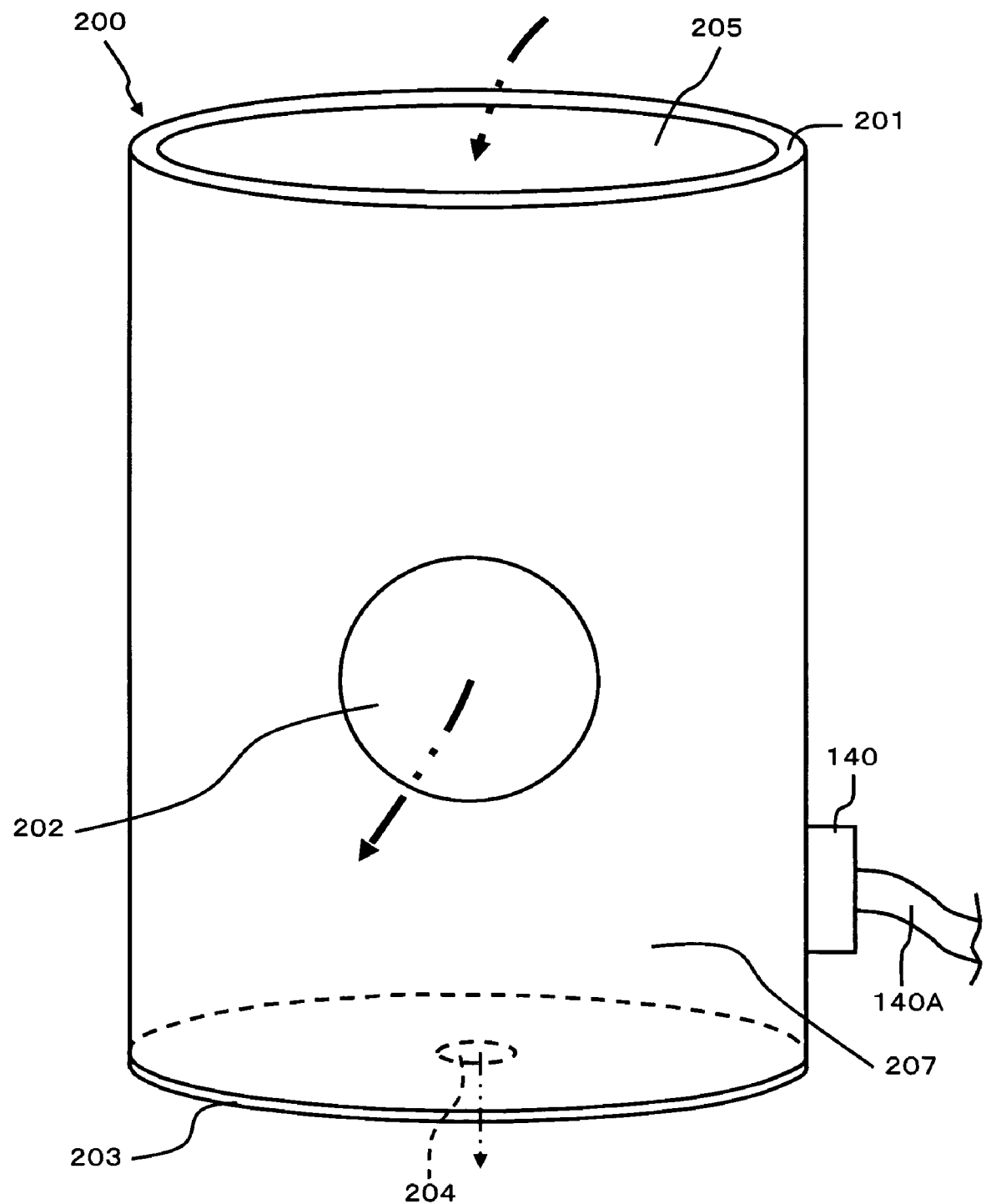
FIG. 15 is a perspective view of the external appearance of a measuring chamber member according to a first variant embodiment.
Figure 16:
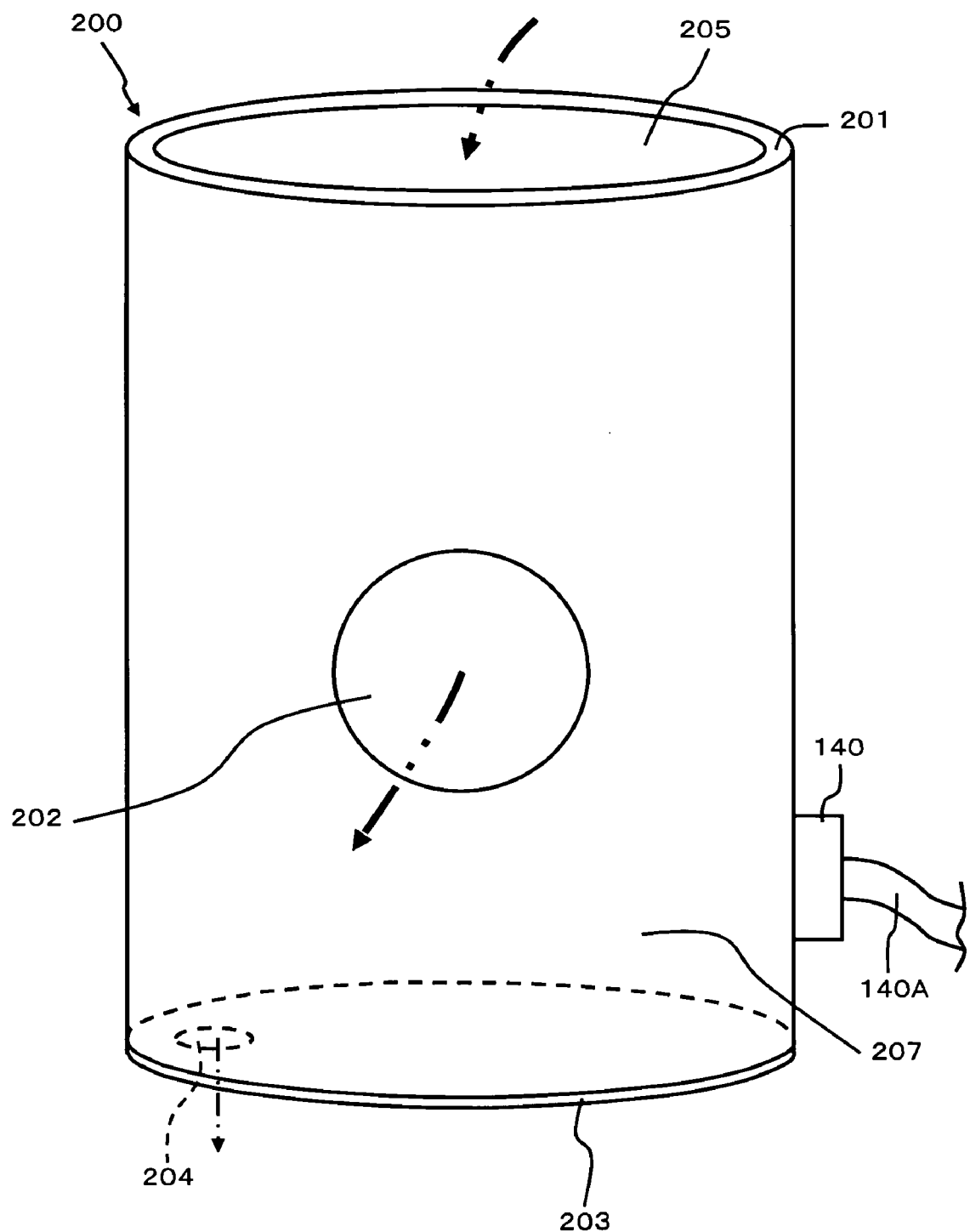
FIG. 16 is a perspective view of the external appearance of a measuring chamber member according to a second variant embodiment.

It should be understood that the embodiments described above are shown only by way of example for explanation of the present invention, and are not intended to limit the range of the present invention in any manner. The present invention may be implemented in various different manners other than the embodiments described above, provided that its gist is not deviated from. For example, it would also be acceptable to arrange to locate the drain aperture 204 in the center of the bottom portion 203, as in a first variant embodiment shown in FIG. 15, or to locate the drain aperture 204 in a position which opposes the fuel property detection sensor 140, as in a second variant embodiment shown in FIG. 16.

Moreover, although examples have been shown in which an inductive type nozzle detection sensor, a photoelectric switch, and a magnetic switch were used as the fuel supply cap sensor 141 for detecting the start or the end of supply of fuel, the present invention is not limited thereto; it would also be possible to use some other type of sensor. For example, it would be acceptable to utilize a reed switch, a mechanical switch, or the like.

The invention claimed is:

1. An apparatus for detecting a property of fuel supplied to an engine of a working machine, wherein the apparatus comprises:
   a measuring chamber provided in an upper area of a fuel tank, wherein the measuring chamber contains a portion of fuel that flows into the fuel tank; and
   a fuel property sensor is provided in association with said measuring chamber, wherein the fuel property sensor detects the property of the fuel and outputs a detection signal,
   wherein said measuring chamber has a top with a fuel supply aperture, and a side with a flow outlet for permitting fuel that has flowed into said measuring chamber from said fuel supply aperture to flow into said fuel tank.

2. The apparatus for detecting a property of fuel supplied to an engine of a working machine according to claim 1, wherein said fuel property sensor detects the property of the fuel contained within said measuring chamber, when a measurement timing has arrived, which is set at a time of supplying fuel into said fuel tank.

3. The apparatus for detecting a property of fuel supplied to an engine of a working machine according to claim 2, wherein said measurement timing is either a fuel supply start timing, at which the supplying of fuel into said fuel tank is started, or a fuel supply end timing, at which the supplying of fuel into said fuel tank is ended.

4. The apparatus for detecting a property of fuel supplied to an engine of a working machine according to claim 2, wherein a cap opening and closing sensor is provided, which detects an open/closed state of a fuel supply cap, wherein said cap covers said fuel supply aperture, and the arrival of said measurement timing is detected on the basis of a signal from the cap opening and closing sensor.

5. The apparatus for detecting a property of fuel supplied to an engine of a working machine according to claim 4, wherein said cap opening and closing sensor detects whether or not said fuel supply cap is on by a non-contact method.

6. The apparatus for detecting a property of fuel supplied to an engine of a working machine according to claim 2, wherein a nozzle sensor is provided in the neighborhood of said fuel supply aperture for detecting whether or not a fuel supply nozzle is inserted into said fuel supply aperture, and the arrival of said measurement timing is determined when the nozzle sensor has detected said fuel supply nozzle.

7. The apparatus for detecting a property of fuel supplied to an engine of a working machine according to claim 2, wherein a remaining fuel amount sensor is provided for detecting an amount of fuel remaining within said fuel tank, and the arrival of said measurement timing is determined when said remaining fuel amount sensor detects an increase of the amount of fuel remaining within said fuel tank.

8. The apparatus for detecting a property of fuel supplied to an engine of a working machine according to claim 2, wherein a cap opening and closing sensor is provided which detects an open/closed state of a fuel supply cap, which caps said fuel supply aperture, and the arrival of said measurement timing is determined if both a state in which said fuel supply cap has been removed and also a state in which it has been fitted have been detected by said cap opening and closing sensor and if said engine has been started.

9. The apparatus for detecting a property of fuel supplied to an engine of a working machine according to claim 2, further comprising
a cap opening and closing sensor for detecting an open/closed state of a fuel supply cap, which caps said fuel supply aperture, and
a remaining fuel amount sensor for detecting an amount of fuel remaining in said fuel tank,
wherein the arrival of said measurement timing is determined if both a state of removal and a state of fitting of said fuel supply cap have been detected by said cap opening and closing sensor and if an increase of the amount of fuel remaining within said fuel tank has been detected by said remaining fuel amount sensor.

10. The apparatus for detecting a property of fuel supplied to an engine of a working machine according to claim 2, wherein the arrival of said measurement timing is determined if said fuel property sensor has detected presence of fuel.

11. The apparatus for detecting a property of fuel supplied to an engine of a working machine according to claim 10, wherein said fuel property sensor is constituted as an optical type fuel property sensor, which detects the property of the fuel on the basis of an index of refraction of a light beam and is adapted to detect the property of the fuel if the presence of fuel has been detected by a change of the refractive index.

12. An apparatus for detecting a property of fuel supplied to an engine of a working machine, wherein the apparatus comprises:
a measuring chamber provided in a fuel tank, wherein the measuring chamber contains a portion of fuel that flows into the fuel tank; and
a fuel property sensor is provided in association with said measuring chamber, wherein the fuel property sensor detects the property of the fuel and outputs a detection signal,
wherein said measuring chamber comprises a tubular main body with a bottom, a fuel supply aperture, which is provided upon an aperture surface of said main body, and a flow outlet, which is provided upon a side surface of said main body, for permitting fuel that has flowed into the measuring chamber from said fuel supply aperture to flow into said fuel tank.

13. The apparatus for detecting a property of fuel supplied to an engine of a working machine according to claim 12, wherein a drain aperture is provided in a bottom portion of said main body, for discharging fuel contained within said main body into said fuel tank.

14. The apparatus for detecting a property of fuel supplied to an engine of a working machine according to claim 13, wherein said fuel property sensor is positioned between said flow outlet and said drain aperture and is fitted to said main body.

15. An apparatus for detecting a property of a liquid fuel supplied to an engine of a working machine, wherein the apparatus comprises:
a measuring chamber, which is located at an inlet arranged in an upper area of a fuel tank, wherein the measuring chamber captures a portion of the fuel that enters the fuel tank through the inlet; and
a fuel property sensor that detects the property of the fuel in the measuring chamber, wherein the fuel property detection device transmits a detection signal to a controller,
wherein said measuring chamber has a bottom with a drain, and a top with a fuel supply aperture, and a side with a flow outlet for permitting fuel that has flowed into said measuring chamber from said fuel supply aperture to flow into said fuel tank.

16. The apparatus according to claim 15, wherein:
the measuring chamber is a container that is located to receive fuel that passes through the inlet of the fuel tank; and
the measuring chamber is constructed and arranged so that fuel passes through the measuring chamber before settling to a bottom of the fuel tank.

17. The apparatus according to claim 15, wherein:
the measuring chamber is a container that is located to receive fuel that passes through the inlet of the fuel tank;
the measuring chamber has an inlet and an outlet; and
the measuring chamber is constructed and arranged to permit passage of fuel through the measuring chamber while delaying the flow of the captured portion of the fuel.

* * * * *